(12) United States Patent
Martin

(10) Patent No.: US 9,782,208 B2
(45) Date of Patent: Oct. 10, 2017

(54) ASSEMBLY COMPRISING AN IMPLANTABLE PART DESIGNED TO BE FASTENED TO ONE OR MORE BONES OR BONE PORTIONS TO BE JOINED, AND AT LEAST ONE SCREW FOR FASTENING THE IMPLANTABLE PART TO SAID BONE(S)

(71) Applicant: Compagnie Financiere et Medicale, Bourg en Bresse (FR)

(72) Inventor: Jean-Jacques Martin, Bourg en Bresse (FR)

(73) Assignee: COMPAGNIE FINANCIERE ET MEDICALE, Bourg en Bresse (FR)

(*) Notice: Subject to any disclaimer, the term of this patent is extended or adjusted under 35 U.S.C. 154(b) by 0 days.

(21) Appl. No.: 14/812,169

(22) Filed: Jul. 29, 2015

(65) Prior Publication Data
US 2015/0327898 A1   Nov. 19, 2015

Related U.S. Application Data

(63) Continuation of application No. 13/604,798, filed on Sep. 6, 2012, now abandoned.

(51) Int. Cl.
*A61B 17/80* (2006.01)
*A61B 17/86* (2006.01)

(52) U.S. Cl.
CPC ...... *A61B 17/8057* (2013.01); *A61B 17/8061* (2013.01); *A61B 17/8066* (2013.01); *A61B 17/86* (2013.01); *A61B 17/863* (2013.01); *A61B 17/8605* (2013.01); *A61B 17/8615* (2013.01); *A61B 17/8625* (2013.01)

(58) Field of Classification Search
CPC ................ A61B 17/7059; A61B 17/80; A61B 17/8033–17/8061; F16B 39/30
See application file for complete search history.

(56) References Cited

U.S. PATENT DOCUMENTS

| 2006/0009771 A1* | 1/2006 | Orbay | A61B 17/8057 606/291 |
|---|---|---|---|
| 2011/0224737 A1* | 9/2011 | Lewis | A61B 17/1728 606/290 |
| 2012/0184959 A1* | 7/2012 | Price | A61B 17/8009 606/70 |

* cited by examiner

*Primary Examiner* — Matthew Lawson
*Assistant Examiner* — Amy Sipp
(74) *Attorney, Agent, or Firm* — Defillo & Associates, Inc.; Evelyn A. Defillo

(57) ABSTRACT

An assembly including an implantable part designed to be fastened to at least one bone or bone portions to be joined and at least one screw for fastening the implantable part to the at least one bone or bone portions. The implantable part includes at least one tapped hole and the screw includes a head designed to be engaged in the tapped hole. The tapped hole is cylindrical and includes at least one radial notch emerging in a surface of the implantable part through which the screw is designed to be engaged in the tapped hole. The radial notch produces an interruption in the tapping included by the tapped hole. The head of the screw is conical, with an apical angle of between 15 and 25°.

8 Claims, 5 Drawing Sheets

ASSEMBLY COMPRISING AN IMPLANTABLE PART DESIGNED TO BE FASTENED TO ONE OR MORE BONES OR BONE PORTIONS TO BE JOINED, AND AT LEAST ONE SCREW FOR FASTENING THE IMPLANTABLE PART TO SAID BONE(S)

CROSS REFERENCE TO RELATED APPLICATION

This application is a Continuation application of U.S. application Ser. No. 13/604,798 filed Sep. 6, 2012, pending, entitled ASSEMBLY COMPRISING AN IMPLANTABLE PART DESIGNED TO BE FASTENED TO ONE OR MORE BONES OR BONE PORTIONS TO BE JOINED, AND AT LEAST ONE SCREW FOR FASTENING THE IMPLANTABLE PART TO SAID BONE(S), the content of which is incorporated herein by reference.

FIELD OF THE INVENTION

The present invention relates to an assembly comprising an implantable part designed to be fastened to one or more bones or bone portions to be joined, and at least one screw for fastening the implantable part to said bone(s). Said implantable part may in particular be a fastening base for fastening part of a joint prosthesis to a bone, in particular a fastening base for fastening a glenoid to shoulder blade in a total shoulder prosthesis; the implantable part may also be a cortical plate or any other piece of arthrodesis or osteosynthesis equipment.

BACKGROUND OF THE INVENTION

It is well known to use screws to fasten implantable parts such as bases used to fasten joint prosthesis components or cortical or similar plates serving to perform an arthrodesis or osteosynthesis of one or more bones.

A very traditional base or plate comprises smooth cylindrical holes in which the fastening screws are designed to be engaged. Each hole may be adjusted to the dimension of the screw designed to be engaged in that hole, thereby defining a single implantation direction of the screw, or may have a diameter larger than that of the screw, to allow implantation of the screw in a plurality of implantation directions.

In the first case, the base of the plate has the drawback of imposing an implantation direction on the screw and therefore prohibiting implantation directions other than that which is imposed. However, depending on the anatomy of the bone or condition of the patient, it may be preferable to implant the screw in a different direction from that of the hole. In the second case, the base or plate does not rule out defective positioning of the screw in relation to the bone(s) in which it is implanted, in particular the risk of the screw emerging at a joint surface of one or more of said bones.

It is also known to arrange a tapping in the hole and a thread on the screw head, the thread of the screw engaging with the tapping of the hole. Such assemblies also have the drawback of imposing an implantation direction on the screw determined by said engagement.

Furthermore, such assemblies have a noteworthy risk of unscrewing of one or more screws over time under the effect of the repeated forces undergone by the bone(s). To resolve this risk of unscrewing, various axial retention systems have been designed for the screws, which, in general, have the drawbacks of being relatively expensive to manufacture and not always being very effective.

Patent application publications nos. US 2010/312286, US 2008/208259 and US 2008/140130 illustrate various techniques of the prior art.

The present invention aims to resolve the aforementioned drawbacks.

The main aim of the invention is to provide an assembly as previously mentioned, in which at least one screw can be implanted in an implantation direction chosen from among several possible implantation directions, and in which the risk of unscrewing of that screw over time is reduced.

Another aim of the invention is to provide an assembly in which the risk of defective positioning of a screw is ruled out, or preserving the possibility of choosing from among several possible implantation directions.

SUMMARY OF THE INVENTION

In the concerned assembly, in a known manner, said implantable part comprises at least one tapped hole, and said screw comprises a head designed to be engaged in said hole.

According to the invention, the hole is cylindrical and comprises at least one radial notch emerging at least in the proximal surface of said implantable part, i.e. in the surface of said implantable part through which the screw is designed to be engaged in the hole, said radial notch producing an interruption in the tapping comprised by the hole;

the head of the screw is conical, with an apical angle comprised between 15 and 25°, and said head is threaded and the pitch of this thread is comprised between one third and one half the pitch of the thread making up the tapping of the hole, and the depth of the thread of that head is comprised between one half and two thirds of the depth of the pitch of the thread making up the tapping of the hole.

The inventor took the opposite course to the fundamental teachings of mechanics, by seeking to engage and jam a screw head with a different shape from that of the hole designed to receive that screw. He was able to determine that the combination of the aforementioned features made it possible to obtain the dual advantageous result of (i) making it possible to engage the screw in a plurality of implantation directions, and (ii) producing, at the end of screwing, effective jamming of the head of the screw in the hole, of a nature to oppose any risk of unscrewing.

The plurality of possible implantation directions of the screw results (i) from the presence of said notch, which locally interrupts the tapping of the hole and allows a slight deformation of said implantable part at that hole, (ii) the specific conical shape of the head, and (iii) the lack of narrow engagement of the respective threats of the head of the screw and hole during the first portion of the screwing phase; said effective jamming also results from (i) said possibility of slight deformation allowed by the notch, (ii) the specific conical shape of the head, which allows the respective threads of the head of the screw and the hole to gradually interlock during the second portion of the screwing phase, and which performs that complete interlocking at the end of screwing.

Preferably, said apical angle is 20°.

The pitch of the thread of the head of the screw is preferably in the vicinity of one half the pitch of the thread of the tapping of the hole.

It was possible to determine these values as optimal to obtain said plurality of implantation and jamming directions of the screw. They allow a possibility of angulation of the axis of the screw in relation to the axis of the hole that may reach 20°.

This axis of the hole may itself not be parallel to a reference plane of the implantable part, for example the general plane in which a cortical plate extends. This angulation of the hole is also added to the angulation of the screw made possible by that hole to allow a significant angulation of the screw in relation to said general plane.

Preferably, said screw comprises a body and a bone screw thread extends along that body into the immediate vicinity of the head of said screw, below said head, such that the proximal end of said screw thread is situated, when the screw is in place on the implantable part, inside said hole.

The presence of said screw thread in the hole contributes to achieving jamming of the screw in the hole.

Preferably, said notch extends over the entire height of the hole.

Said slight deformation of the implantable part at that notch is thus made completely possible.

Preferably, the hole comprises a plurality of notches.

According to one possibility, said notches may be present over the entire circumference of the hole, allowing an angulated orientation of the screw over the entire circumference. They may particularly be regularly distributed on that circumference.

According to another possibility, these notches are present on a first sector of the circumference of the hole and absent on a second sector of the circumference of said hole.

An angulated orientation of the screw is thus prohibited on the side of the hole opposite that on which said second sector is located. Due to this possibility for selective angulation of the screw, resulting from the arrangement of the notches in carefully chosen locations of the holes, an implantable part may be produced making it possible to protect against the risk of defective implantation of the screw, in particular the risk of a screw emerging at a joint surface of one or more of the treated bones.

This possibility may in particular be implemented on a shoulder prosthesis glenoid base, to orient an anchoring screw in the pillar of the coracoid and the pillar of the shoulder blade. This possibility may also be implemented on cortical plates whereof one end is designed to be implanted near a joint surface formed by a bone, in particular on an upper humeral plate or a lower radial plate.

BRIEF DESCRIPTION OF THE DRAWINGS

The invention will be well understood, and other features and advantages thereof will appear, in reference to the appended diagrammatic drawing, showing, as non-limiting examples, several possible embodiments of the implantable part-screw assembly to which it pertains.

DETAILED DESCRIPTION OF THE EMBODIMENT OF THE INVENTION

Figure 1:
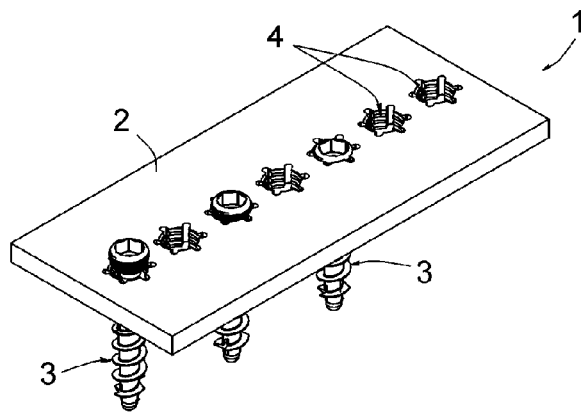
FIG. 1 is a perspective view of the plate comprising a series of holes in which anchor screws for anchoring that plate are designed to be received.

FIG. 1 shows an assembly 1 comprising an implantable part 2 designed to be fastened to one or more bones or bone portions to be joined, and several screws 3 for fastening said implantable part 2 to said bone(s).

Figure 11:
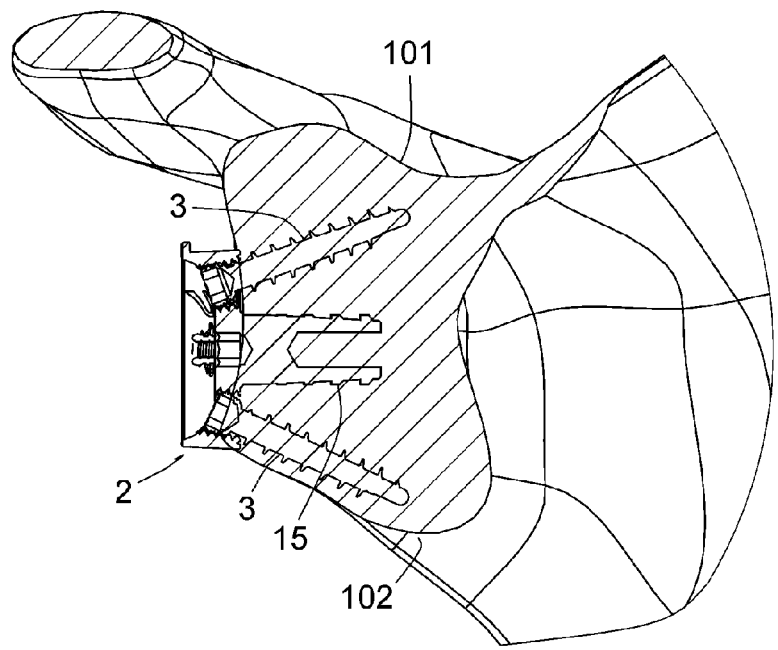
FIG. 11 is a front cross-sectional view of part of a shoulder blade in which a base for receiving a glenoid has been implanted.
Figure 12:
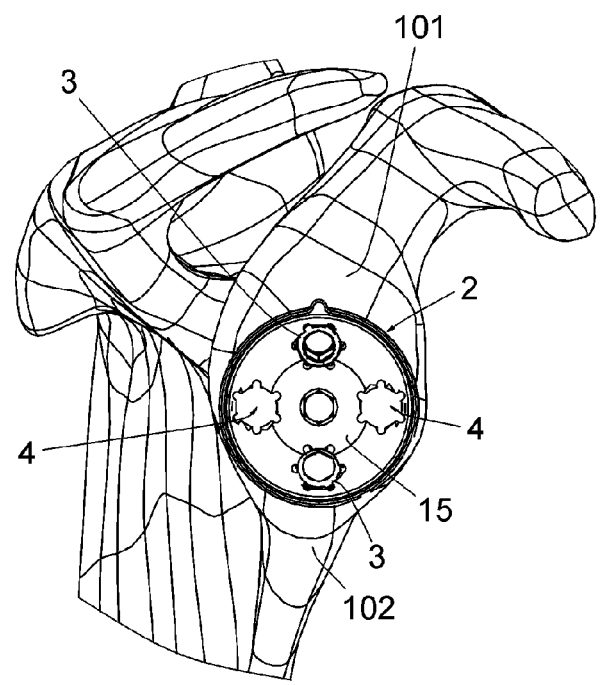
FIG. 12 is a sagittal view of the portion of the shoulder blade, along the axis of said base.
Figure 13:
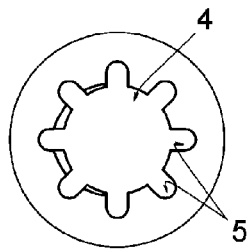
FIGS. 13 to 18 are front views of six possible embodiments of a hole comprised by the implantable part according to the invention.
Figure 14:
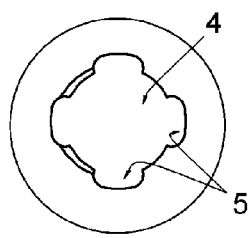
Figure 15:
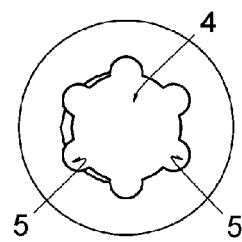
Figure 16:
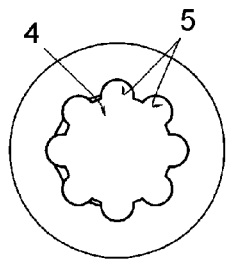

For the purposes of a purely diagrammatic illustration, the implantable part 2 has been shown in FIG. 1 as a rectangular plate with any shape whatsoever. FIGS. 11 and 12 show that this implantable part may be a base 2 for fastening a glenoid to a shoulder blade 100 or a part forming a convex joint surface called "metaglene" or "glenosphere" (not shown); this implantable part may also be a humeral cortical plate 2 (cf. FIGS. 19 and 20) or cortical plate for the lower end of the radius (cf. FIGS. 21 to 23).

The plate 2 shown in FIG. 1 comprises a plurality of aligned holes 4, each of which is designed to receive a screw 3.

Figure 2:
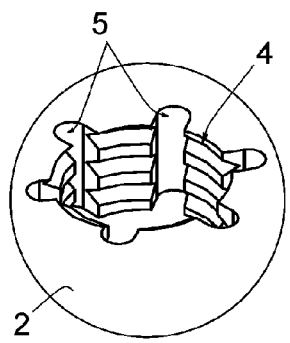
FIG. 2 is an enlarged perspective view of one of the holes.
Figure 3:
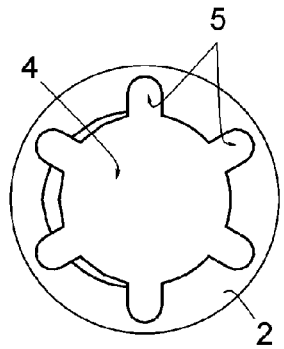
FIG. 3 is a front view of the hole.

As shown more particularly in FIGS. 2 and 3, each hole 4 is cylindrical and tapped, and comprises six notches 5 extending radially, regularly distributed around its circumference. These notches 5 extend over the entire thickness of the plate 2 and consequently interrupt the screw pitch of the tapping of the hole 4 over the entire height thereof. They are substantially U-shaped, i.e. each one forms two radial surfaces opposite one another and a rounded bottom connecting those two surfaces.

Figure 4:
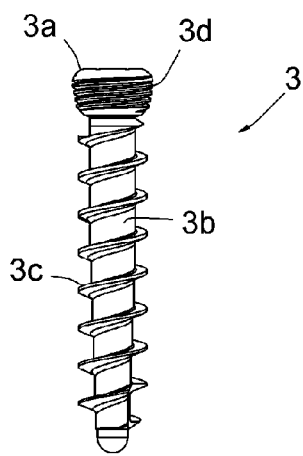
FIG. 4 is a side view of a screw.
Figure 5:
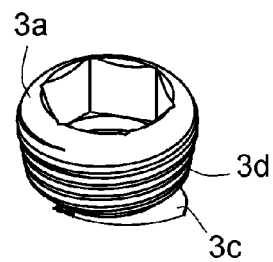
FIG. 5 is an enlarged perspective view of the head of said screw.
Figure 6:
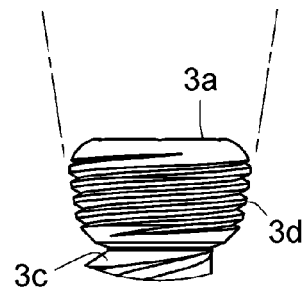
FIG. 6 is an enlarged side view of said head.

In reference to FIGS. 4 to 6, it appears that the screw 3 comprises a conical and threaded head 3a, and a body 3b provided with a screw thread 3c adapted for bearing in a bone.

The apical angle of the cone defining the head 3a is 20° (cf. FIG. 6). The pitch of the screw thread of that head 3a is in the vicinity of one third of the pitch of the tapping of a hole 4, and the depth of the screw thread is in the vicinity of one half that of the pitch of the tapping of a hole 4.

The screw thread 3d of the head 3a is symmetrical, has flanks that may be inclined between 45° and 75°, and has an identical depth over the entire length of the head. The screw thread may be a dual entry screw thread.

The bone screw thread 3c comprised by the body 3b of the screw extends along said body into the immediate vicinity of the head 3a, and is interrupted immediately below that head 3a.

Figure 7:
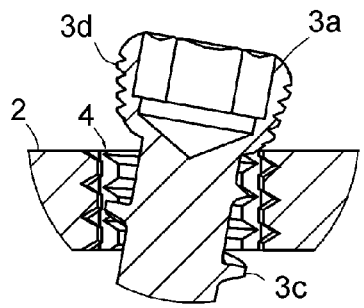
FIGS. 7 to 9 are partial cross-sectional views of the plate and the screw, during three successive phases of placing the screw in the hole.

Each screw 3 is designed to be engaged in a hole 4 and to be screwed in the bone(s) to which the plate 2 is designed to be fastened. The screws 3 may be engaged in the holes 4 perpendicular to the plate 2, as shown by FIG. 1, or maybe placed in said holes 4 not perpendicular to the plate 2, as appears in FIGS. 7 to 9.

Figure 8:
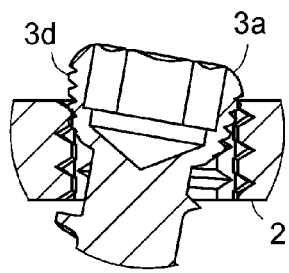

This possibility for the angulation of the screw 3, and therefore of a plurality of possible implantation directions of that screw, results (i) from the presence of the notches 5, which locally interrupt the tapping of the hole 4 and allow a slight deformation of the part 2 at that hole 4, (ii) the aforementioned conical shape of the head 3a, and (iii) the absence of narrow engagement of the respective screw threads of the head 3a of the screw 3 and the hole 4 during the first part of the screwing phase, i.e. substantially at the position of the screw 3 shown in FIG. 8.

Figure 9:
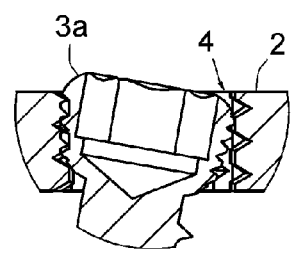

From this position, and in a second portion of the screwing phase going as far as the end of screwing position shown in FIG. 9, progressive and effective jamming of the head 3a occurs in the hole 4, of a nature to oppose any risk of unscrewing of the screw 3. This jamming results from (i) said possibility of slight deformation allowed by the notches 5, and (ii) the aforementioned conical shape of the head 3a, which allows the gradual interlocking of the respective threads of the head 3a and the hole 4 during said second portion of the screwing phase, and which performs the complete interlocking at the end of screwing.

It will also be understood in reference to FIG. 9 that the portion of the first turn of the bone screw thread 3c can be located, in that end-of-screwing position, inside the hole 4, thus contributing to the jamming of the screw 3 in said hole 4.

Figure 10:
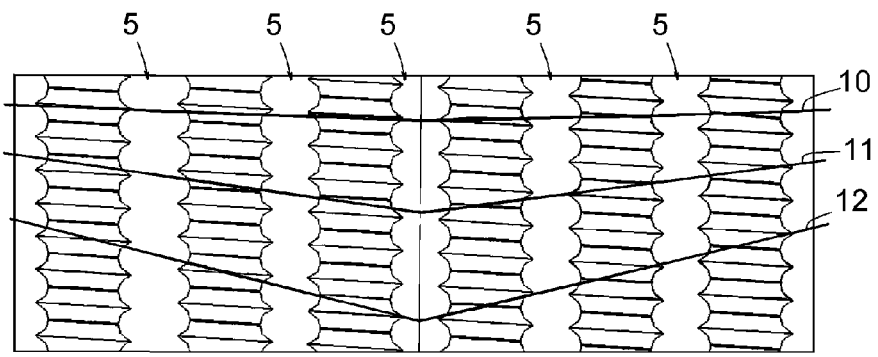
FIG. 10 is a developed view of the hole, with a diagrammatic indication of the position of the turn of the thread of the screw according to three angulations, showing an absence of screw thread jump.

FIG. 10 shows the development of the hole 4 with three lines 10, 11, 12 each representing the development of a turn of the screw thread 3d of the head 3a, for respective angulations of the screw 3 of 0°, 6° and 12°. It shows that there is no screw thread jump.

In reference to FIGS. 11 and 12, it appears that the aforementioned base 2 comprises a central anchor lug 15 and four holes 4 distributed around said lug 15, designed to receive screws 3 (only two of the four screws 4 are placed on the illustrated base 2, for which placement is in progress).

It appears that the axes of the holes 4 are not parallel to the axis of the lug 15, but rather inclined in relation to the axis, by 10° in the illustrated example. This angulation of the holes 4 is thus added to the angulation of the screws 3 made possible by those holes, so as to allow a significant angulation of the screws 3 in relation to a reference plane perpendicular to the axis of the lug 15. In the illustrated example, the total angulation of the lower screw 3 is 20° (10° angulation of the hole 4 in relation to said axis, and 10° angulation of the screw 3 in the hole 4). Owing to this possibility of significant angulation, the upper screw 3 and the lower screw 3 can be oriented optimally for anchoring respectively in the pillar 101 of the coracoid and the pillar 102 of the shoulder blade.

FIGS. 13 to 16 show holes 4 having shapes and numbers of notches 5 different from those described above. The hole 4 shown in FIG. 13 comprises notches identical to those described above, but comprises eight instead of six. The hole 4 shown in FIG. 14 comprises only four notches 5, also U-shaped, but much wider than those described above. The hole 4 shown in FIG. 15 comprises six notches 5 with a half-circle section. The hole 4 shown in FIG. 16 comprises eight such notches 5 with a half-circle section.

Figure 17:
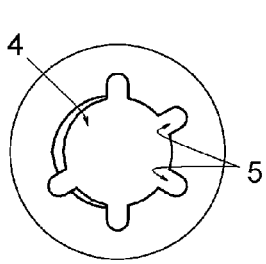
Figure 18:
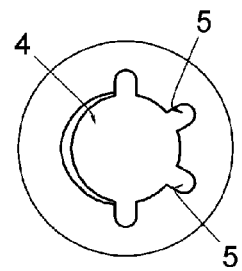

The hole 4 shown in FIG. 17 comprises five notches 5 regularly arranged on a first sector in the vicinity of 240° and is provided without notches on a second sector in the vicinity of 120°. Similarly, the hole 4 shown in FIG. 18 comprises four notches 5 regularly arranged on the first sector in the vicinity of 180° and is provided without notches on the second sector in the vicinity of 180°. The absence of notches 5 on said second sectors amounts to a rigidity of the implantable part 2 and continuity of the screw thread of the tapping of the hole 4 at said second sectors, which results in an impossibility of orienting the screw 3 on the sides of the holes 4 opposite those on which said second sectors are located.

Implantable parts 2 may thus be designed whereof the risk of defective implantation of a screw 3 is eliminated.

Figure 19:
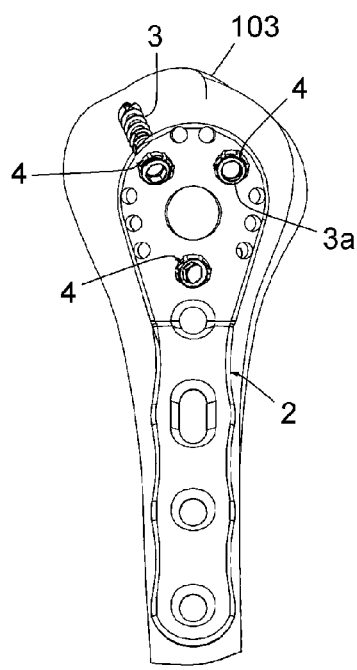
FIGS. 19 and 20 are sagittal and anterior views, respectively, of the upper portion of the humerus on which a plate according to the invention has been placed.
Figure 20:
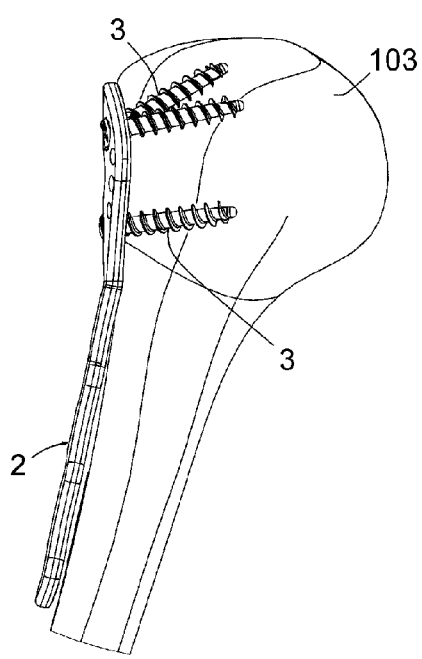

Thus, in reference to FIG. 19, it appears that a humeral plate 2 may comprise, in the epiphyseal portion thereof, two side-by-side holes 4 whereof the sectors facing the side opposite the epiphyseal end of said plate 2 are provided without notches. Then, an excessive orientation of the screws 3 toward the epiphyseal cortical bone of the humeral head 103 is prevented, as shown in FIG. 20, which avoids the risk of said screws 3 emerging on the joint surface of the humerus. The third hole 4 comprised by said epiphyseal portion also has a sector provided without notches on the side of that hole opposite the epiphyseal end of the plate 2; said sector thus prevents the orientation of the screw 3 engaged in that hole toward the humeral diaphysis. However, the possibility remains of choosing the implantation direction of the screws 3 in the other directions mentioned above.

Figure 21:
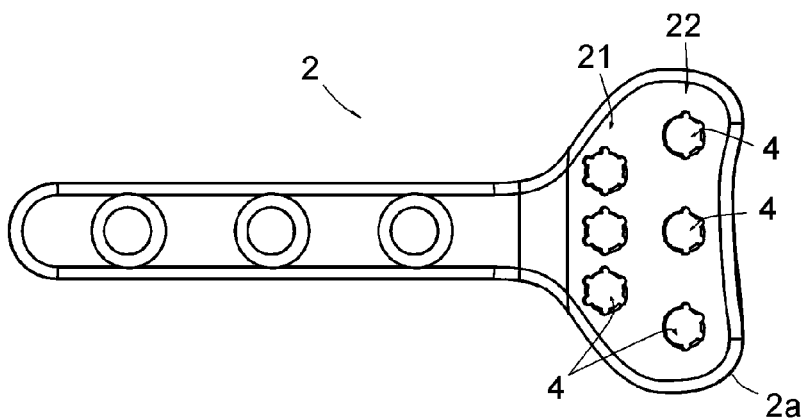
FIG. 21 is a top view of a plate for the lower end of the radius.

FIG. 21 shows a plate 2 for a lower end of the radius, traditionally having a widened distal portion 2a. In that distal portion 2a, a proximal series 21 of four holes 4 and a distal series 22 of three holes 4 are arranged transversely. The holes 4 of the proximal series 21 each comprise six notches as described above, allowing a multidirectional orientation of the screws 3. Each hole 4 of the distal series 22 comprises a first sector having four notches 5, turned toward the distal end of the plate 2, and a second sector provided without notches, situated on the side of the hole 4 turned toward the side of said proximal series 21.

Figure 22:
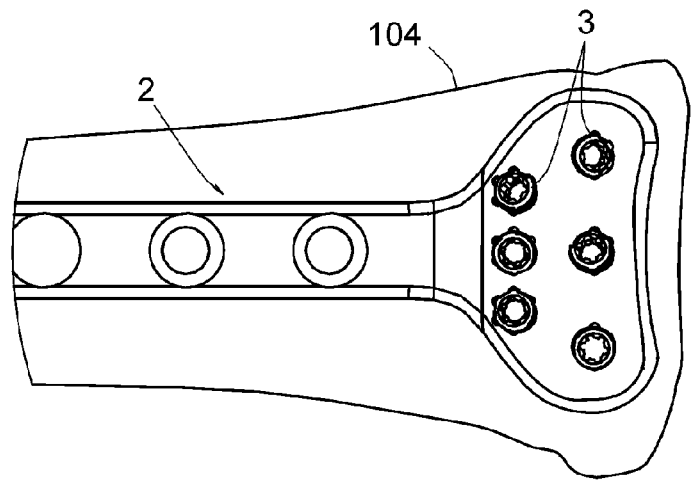
FIGS. 22 and 23 are top and side views, respectively, of said plate, after placement on a radius.
Figure 23:
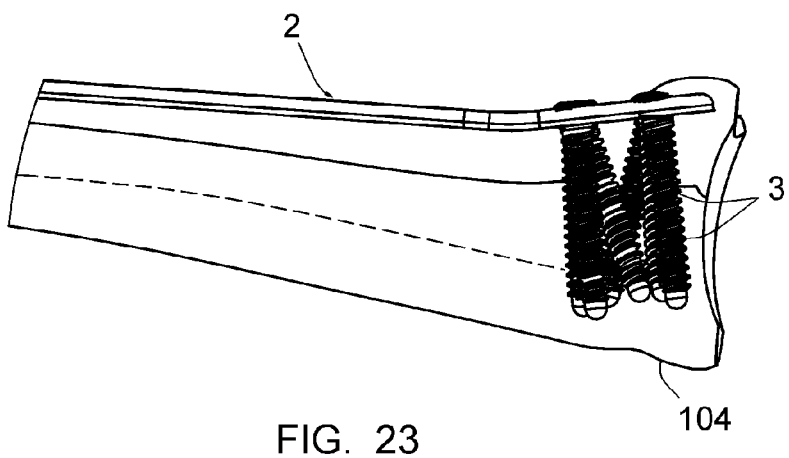

As will be understood in reference to FIGS. 22 and 23, the screws 3 engaged in the holes 4 of the distal series 22 may not be oriented toward the distal end of the radius 104, which prevents any risk of said screws 3 emerging at the joint surfaces comprised by said radius 104.

It appears from the preceding that the invention provides an assembly 1 including an implantable part 2 and at least one screw 3, having the decisive advantages of making it possible to engage the screw 3 in a hole 4 of the part 2 in a plurality of implantation directions, and of achieving, at the end of screwing, effective jamming of the head 3a of the screw in the hole 4, of a nature to oppose any risk of unscrewing. Another decisive advantage of this assembly 1 is making it possible to eliminate the risk of defective positioning of the screw 3.

The assembly 1 according to the invention can be used on all anatomies other than those previously mentioned, such as femur, tibia, elbow or foot, and works irrespective of the material used, for example stainless steel or titanium.

The invention was described above in reference to embodiments provided as examples. It is of course not limited to these embodiments, but on the contrary encompasses all other embodiments covered by the appended claims. In particular, the base 2 shown in FIGS. 11 and 12 can comprise middle holes 4 (i.e. the two holes 4 other than the upper hole and the lower hole visible in FIG. 12) provided without notches 5 on the sectors thereof turned toward the outside of the base 2, thereby prohibiting the screws from being oriented in implantation directions that risk causing those screws to emerge outside the bone.

What is claimed is:

1. An assembly comprising:
an implantable part configured to attach to at least one bone or bone portions to be joined, the implantable part includes a first face directly contacting the at least one bone or bone portion when said implantable part is implanted, a second face being opposed to the first face, and at least one tapped hole, each tapped hole extending through an entire thickness of the implantable part connecting the first face and the second face;
at least one screw for fastening the implantable part to the at least one bone or bone portions, and each screw of the at least one screw includes a head designed to be engaged in one of said tapped hole;
wherein:
each tapped hole is cylindrical, internally threaded, and includes a plurality of notches, each notch of the plurality of notches extending through an entire thickness of the tapped hole from the first face to the second face of the implantable part, each notch of the plurality of notches emerging in a surface of the tapped hole;
said plurality of notches produce an interruption in the internal thread of the tapped hole;
the head of the at least one screw forms a main peripheral surface which is conical, with an apical angle comprised between 15 and 25°;
said main peripheral surface of the head is externally threaded with a pitch that is between one third and one half of a pitch of the internal thread of the tapped hole, and a depth of the external thread of said main peripheral surface of the head includes between one half and two thirds of a depth of the thread of the tapped hole;
each tapped hole of the at least one tapped hole includes a circumference with a first section and a second section opposite to the first section and in the vicinity of 180 degrees, said first section of the circumference of each tapped hole includes the plurality of notches, said second section of the circumference of the tapped hole is free of the plurality of notches.

2. The assembly according to claim 1, wherein said apical angle is 20°.

3. The assembly according to claim 1, wherein the pitch of the thread of the head of the at least one screw is substantially one half of the pitch of the thread of the tapping of the tapped hole.

4. The assembly according to claim 1, wherein said at least one screw comprises a body and a bone screw thread extends along that body substantially to said head of said at least one screw, such that a proximal end of said external thread of the main peripheral surface of the head of said at least one screw is situated inside said tapped hole, when the screw is in place on the implantable part.

5. The assembly according to claim 1, wherein said implantable part is a fastening base for fastening part of a joint prosthesis to a bona the at least one bone or bone portions.

6. The assembly according to claim 1, wherein said implantable part is a fastening base for fastening to a glenoid to shoulder blade in a total shoulder prosthesis.

7. The assembly according to claim 1, wherein said implantable part is a cortical plate, a superior humeral cortical plate, or an inferior radius cortical plate.

8. An assembly comprising:
an implantable part configured to attach to at least one bone or bone portions to be joined, the implantable part includes a first face directly contacting the at least one bone or bone portion when said implantable part is implanted, a second face being opposed to the first face, and at least one tapped hole, each tapped hole extending through an entire thickness of the implantable part connecting the first face and the second face;
a central anchor lug placed on the implantable part, the central anchor lug having an axis;
at least one screw for fastening the implantable part to the at least one bone or bone portions, and each screw of the at least one screw includes a head designed to be engaged in one of said tapped hole;
wherein:
the tapped holes are distributed around the central anchor lug and each tapped hole includes an axis;
the axis of the tapped holes is not parallel to the axis of the central anchor lug;
each tapped hole is cylindrical, internally threaded, and includes a plurality of notches, each notch of the plurality of notches extending through an entire thickness of the tapped hole from the first face to the second face of the implantable part, each notch of the plurality of notches emerging in a surface of the tapped hole;
said plurality of notches produces an interruption in the internal thread of the tapped hole;
the head of the at least one screw forms a main peripheral surface which is conical, with an apical angle comprised between 15 and 25°;
said main peripheral surface of the head is externally threaded with a pitch that is between one third and one half of a pitch of the internal thread of the tapped hole, and a depth of the external thread of said main peripheral surface of the head includes between one half and two thirds of a depth of the thread of the tapped hole;
each tapped hole includes a circumference with a first section and a second section opposite to the first section and in the vicinity of 180 degrees, said first section of the circumference of each tapped hole includes the plurality of notches, said second section of the circumference of the tapped hole is free of the plurality of notches.

* * * * *